United States Patent [19]

Maksem

[11] Patent Number: 4,857,300

[45] Date of Patent: Aug. 15, 1989

[54] CYTOLOGICAL AND HISTOLOGICAL FIXATIVE FORMULATION AND METHODS FOR USING SAME

[75] Inventor: John A. Maksem, Cleveland Heights, Ohio

[73] Assignee: Cytocorp, Inc., Cleveland, Ohio

[21] Appl. No.: 78,376

[22] Filed: Jul. 27, 1987

[51] Int. Cl.$^4$ .............................................. G01N 1/30
[52] U.S. Cl. ............................................ 424/3; 435/1; 435/4; 435/29
[58] Field of Search ....................... 424/3; 435/4, 1, 29

[56] References Cited

U.S. PATENT DOCUMENTS

| | | | |
|---|---|---|---|
| 3,862,300 | 1/1975 | Wertlake et al. | 424/3 |
| 4,595,524 | 6/1986 | Yip et al. | 424/3 |

FOREIGN PATENT DOCUMENTS 0159603  10/1985  European Pat. Off. ................ 424/3

*Primary Examiner*—Robert J. Warden
*Assistant Examiner*—Stephen C. Wieder
*Attorney, Agent, or Firm*—Jones, Day, Reavis & Pogue

[57] ABSTRACT

A unique cytologic and histologic fixative formulation and methods for using that formulation are disclosed. The formulation fixes and preserves individual cells, aggregates of cells and small fragments of tissue in a liquid suspension; minimizes protein precipitation in the liquid suspension; selectively eliminates or reduces red blood cell contamination of cytologic material and cytologic specimen slides; retains tissue samples that are incidentally collected along with cytologic material for further histologic processing; and allows shipment of cytologic material under conditions typically encountered in postal carriage, permitting remote users without available cytologists, cytotechnologists or other personnel experienced in the preparation of cytologic samples to have technically satisfactory cytologic sample slides, and which formulation comprises in combination:

(a) N,N-dimethylformamide, about 10 to about 50 percent by volume;

(b) an alcohol, from about 0 to about 50 percent by volume;

(c) water or other diluent, from about 80 to about 0 percent by volume;

(d) formalin, from about 0 to about 3 percent by volume;

(e) polyethylene glycol, from about 0 to about 10 percent by volume; and (f) a tertiary amine or other suitable buffer solution having pH greater than about 7.6, from about 0 to about 2 percent by volume.

3 Claims, No Drawings

CYTOLOGICAL AND HISTOLOGICAL FIXATIVE FORMULATION AND METHODS FOR USING SAME

BACKGROUND OF THE INVENTION

1. Field of the Invention

The present invention relates to the fields of cytopathology and histology and, more specifically, to an improved cytologic and histologic fixative formulation for fixing cells, cell aggregates and small tissue fragments for the examination of same and for the diagnosis of disease.

2. Description of the Prior Art

Properly fixing (i.e., preserving) cytologic material such as cells, cell aggregates and small tissue fragments derived from cytologic collections of human or animal tissue is a prerequisite to the accurate diagnosis of disease, especially cancer. Cytologic material must be fixed as soon as possible after obtaining the material to prevent cell distortion.

Cytologic specimens, which constitute the examinable form of the cytologic material, may be prepared by well-understood smear or fluid techniques. Because there may be a considerable lapse of time before these specimens are further processed by staining, coverslipping, and so forth, however, it is important to apply a fixative to the cytologic material as a means of preserving and fixing the cells.

Air-dried and tetrachrome-dye stained cytologic specimens, although popular abroad, are not generally used in the United States. Rather, wet fixation, either by the immersion of slides into an alcohol solution, by saturation of slides with a spray fixative or by directly discharging cytologic material into an alcohol solution, is a knowm method of cell fixation. Cell fixation is a prerequisite for interpretable Papanicolaou, Hematoxylin and Eosin or other stained cytologic specimen slides.

Generally, alcohol solutions, with or without other additives such as polyethylene glycol, ranging from 50% to 95% (v/v: methanol, ethanol, isopropanol) are known solutions for use in wet fixation. When alcohol solutions greater than 50% (v/v) are used for collecting and fixing fluids high in protein, however, a protein sediment forms which subsequently hardens. Protein sedimentation makes the fixed cytologic material difficult to transfer to glass slides for examination, regardless of whether the transfer is done by direct application to the glass slide, by cytofiltration through a small pore filter, or by cytocentrifugation onto glass slides coated with an adhesive such as chrome alumn gelatin.

The preparation of a technically satisfactory cytologic specimen usually requires the skill of a trained cytologist, cytotechnologist or physician. See generally, Zajicek, J., "The Aspiration Biopsy Smear" in Diagnostic Cytology and its Histopathologic Bases, 3rd Ed. Koss, L. G., Editor (Philadelphia: J. B. Lippincott), Vol. 2, Chapter 29. According to the Zajicek article, when the collection of cytologic material is performed by suspending the cytologic material in an alcohol solution, however, less skill is required and technical problems are diminished.

Cytologic material with a high red blood cell content dilutes the cell population of diagnostic interest by red blood cells. Methods have been used to decolorize the red blood cells in such cytologic specimens such as post-fixation of the cytologic specimen slide in Carnoy's solution comprising 60% ethanol, 30% chloroform and 10% glacial acetic acid (v/v). Such post-fixation of the cytologic specimen slide creates the additional problem of diluting the number of diagnostic cells on the cytologic specimen slide.

Many cytologic specimens such as fine needle aspiration biopsies, brushings or scrapings of tissues and other such specimens consist of admixed tissue fragments and cells. Alcohol fixatives are not optimum fixatives for cytologic specimens containing tissue fragments because the processed tissue fragments become distorted in their appearance. Indeed, there is an advantage to examining both cells and tissue fragments obtained from cytologic specimens. See, Maksem, J. A., et al. "Aspiration Cytology and Transmission Electron Microscopy (TEM): A Novel Tissue Collection Technique With Useful Diagnostic Applications," Proceedings E.M.-S.A., 42, 90–93 (1984). See also, Yamamoto, R., et al. "Histocytologic Diagnosis of Pancreatic Cancer by Percutaneous Aspiration Biopsy Under Ultrasonic Guidance," Am. J. Clin. Pathol., 83, 409–414 (1985).

Other sources have reported the advantages of working with cells collected in suspension. See Alfthan, O., et al., "Cytological Aspiration Biopsy and Vim-Silverman Biopsy in the Diagnosis of Prostatic Carcinoma," Chir. Gynaec. Fenn., 59 226–229 (year). See also, Smith, M. J., et al., "Fine Needle Aspiration and Endoscopic Brush Cytology," Acta Cytol., 456–459 (1980); Saccomanno, G., Diagnostic Pulmonary Cytology (Chicago: American Society of Clinical Pathologists) (1978).

Moreover, alcohol-free suspensions which are the most versatile cannot be stored for a long amount of time or transported over long distances. See, Boon, M. E. and Lykles, C., "Imaginative Approach to Fine Needle Aspiration Cytology," Lancet, 1031–1032 (1980).

It is thus an object of this invention to provide a cytologic and histologic fixative formulation that fixes and preserves cells, cell aggregates and small tissue fragments in a liquid suspension.

It is yet another object of this invention to provide a fixative formulation that minimizes protein precipitation in the liquid suspension.

It is indeed another object of this invention to provide a fixative formulation that selectively eliminates or reduces red blood cell contamination of cytologic material.

It is still another object of this invention to provide a fixative formulation that retains tissue samples which are incidentally collected along with cytologic material for further histological processing.

It is yet a further object of this invention to provide a fixative formulation that allows shipment of the liquid suspension of cells, cell aggregates and tissue fragments under conditions typically encountered in postal carriage, permitting remote users without available cytologists, cytotechnologists, physicians or other personnel experienced in the preparation of cytologic samples to fix a cytologic specimen for later processing, and whereby technically satisfactory cytologic sample slides may be produced therewith.

SUMMARY OF THE INVENTION

A fixative formulation, having a pH of greater than about 7.6, for fixing and preserving individual cells, aggregates of cells and small fragments of tissue in a liquid suspension; for minimizing protein precipitation in the liquid suspension; for selectively eliminating or reducing red blood cell contamination of the liquid suspension; for retaining small tissue fragments derived from cytologic material collection procedures for later examination; for preserving the fixed liquid suspension of cells, cell aggregates and small tissue fragments for periods of time and under conditions typically encountered in postal carriage, comprising in combination:
(a) N,N-dimethylformamide, about 10 to about 50 percent by volume;
(b) an alcohol, from about 0 to about 50 percent by volume;
(c) water or other diluent, from about 80 to about 0 percent by volume;
(d) formalin, from about 0 to about 3 percent by volume;
(e) polyethylene glycol, from about 0 to about 10 percent by volume; and
(f) a tertiary amine or other suitable buffer solution having pH greater than about 7.6, from about 0 to about 2 percent by volume.

DETAILED DESCRIPTION OF THE INVENTION

A fixative formulation for fixing and preserving individual cells, aggregates of cells and small fragments of tissue comprising:
(a) N,N-dimethylformamide, about 10 to about 50 percent by volume;
(b) an alcohol, from about 0 to about 50 percent by volume;
(c) water or other diluent, from about 80 to about 0 percent by volume;
(d) formalin, from about 0 to about 3 percent by volume;
(e) polyethylene glycol, from about 0 to about 10 percent by volume; and
(f) a tertiary amine or other suitable buffer solution having pH greater than about 7.6, from about 0 to about 2 percent by volume.

When applied to cytologic material, the advantages of the fixative formulation of the present invention and its method for using it are as follows. It generates a highly reproducible cytologic specimen slide and eliminates the necessity of on-site cytologic specimen slide preparation. It further permits the transfer of full control of slide preparation and processing to the cytopathology laboratory. Finally, the cytologic material once fixed is of such a quality that cannot be reproducibly achieved by commonly available methods.

Table 1 summarizes the range of concentrations as well as the preferred concentrations (by volume) of the components of the fixative formulation of the present invention.

TABLE 1

| CHEMICAL | PREFERRED | RANGE |
| --- | --- | --- |
| N,N—dimethylformamide | 30% | 10–50% |
| Alcohol | 10% | 0–50% |
| Formalin | 1% | 0–3% |
| Polyethylene glycol | 0% | 0–10% |
| Water or other diluent | 58.9% | 80–0% |
| Tertiary amine | 0.1% | 0–2% |

As shown in Table 1, N,N-dimethylformamide in the amount of about 10 to about 50 percent by volume is one component of the fixative formulation. About 30 percent by volume is preferred in the formulation.

As further shown in Table 1, an alcohol, from about 0 to about 50 percent by volume may also be used in the formulation. Primary (ethanol, methanol, for example) alcohols and secondary (isopropanol, for example) alcohols may be used. As one skilled in the art would know, others may also be substituted. About 10 percent by volume of alcohol is preferred in the formulation.

Formalin, from about 0 to about 3 percent may also be used in the formulation. Formalin is formaldehyde, a commercial preparation of about 37 percent by weight; the balance is water with a small amount of methanol. About one percent by volume is preferred in the formulation.

Polyethylene glycol, from about 0 to about 10 percent, may also be used, principally as a diluent. In the preferred formulation, none is used. It may be used, however, in an amount not exceeding about 10 percent in the formulation.

Water or other diluent is also used in an amount of about 80 to about 0 percent by volume. Any suitable diluent that does not change the important chemical and physical characteristics of the formulation may be used. About 59 percent of water or other diluent is preferred in the formulation.

Finally, any tertiary amine or triethyl amine or other buffer solution having buffering capability at pHs greater than about 7.6 is an element of the formulation, in an amount from about 0 percent to about 2 percent. It is believed important for the quality of the specimen produced to use an amine or other buffer solution having buffering capability at pHs greater than about 7.6 but less than about 10.0, and the resultant formulation has a pH ranging from about 7.6 to about 10.0. Triethyl amine in an amount of 0.1 percent is preferred in the formulation.

The collection of cells and small tissue fragments is performed by any one of the number of well known techniques including any of the following techniques: direct scrapings, brushings, collection and concentration of a fluid specimen with a standard preparatory centrifuge, fine needle aspiration biopsy or any other known method.

The collected cytologic material is suspended in a balanced salt solution such as 0.9% NaCl in water, Ringer's solution or any similar balanced salt solution. As is well known, any volume may be used, but a sufficient volume (as is necessary to suspend the sample) is normally used. If the cytologic material is collected in a body fluid, the cytologic material is separated from the body fluid by the use of a preparative centrifuge and is then suspended in a balanced salt solution.

The suspension is diluted and fixed by adding from about 2 to about 3 volumes of the fixative formulation to the suspended cytologic material.

The fixative formulation may be used for the fixing and preserving of cytologic material and for the preparation of cytologic specimen and histologic specimen slides.

As one skilled in the art would appreciate, many variations, modifications and changes may be made to the compositions and methods of the present invention which do not depart from the spirit and scope of the invention.

I claim:
1. A method for the preparation of a cytologic specimen slide comprising the following steps:
(a) collecting a cell sample;
(b) suspending the cell sample in a suitable volume of balanced salt solution and fixing that suspended cell sample by adding about 2 to about 3 volumes of a fixative formulation comprising:
  (i) N,N-dimethylformamide, about 10 to about 50 percent by volume;
  (ii) an alcohol, from about 0 to about 50 percent by volume;
  (iii) water or other diluent, from about 80 to about 0 percent by volume;
  (iv) formalin, from about 0 to about 3 percent by volume;
  (v) polyethylene glycol, from about 0 to about 10 percent by volume; and
  (vi) a tertiary amine or other suitable buffer solution having pH greater than about 7.6, from about 0 to about 2 percent by volume, and;
(c) applying the fixed, suspended sample to a slide at any time after fixation.

2. A fixative formulative comprising:
(a) N,N dimethylformamide, about 10 to about 50 percent by volume;
(b) an alcohol, from about 0 to about 50 percent by volume;
(c) water or other diluent, from about 80 to about 0 percent by volume;
(d) formalin, from about 0 to about 3 percent by volume;
(e) polyethylene glycol, from about 0 to about 10 percent by volume, and;
(f) a tertiary amine or other suitable buffer solution having pH greater than about 7.6, from about 0 to about 2 percent by volume.

3. A fixative formulation comprising in combination:
(a) About 30 percent by volume N,N-dimethylformamide;
(b) About 10 percent by volume of an alcohol;
(c) About 1 percent by volume formalin;
(d) About 0.1 percent by volume of a tertiary amine, and;
(e) About 58.9 percent by volume of water or other diluent.

* * * * *